United States Patent [19]
Jonjic

[11] Patent Number: 5,904,689
[45] Date of Patent: May 18, 1999

[54] SURGICAL ANGLED SCREWDRIVER

[76] Inventor: Leo Jonjic, Primorska 31, 51414, Ika-Icici, Croatia

[21] Appl. No.: 08/949,908

[22] Filed: Oct. 14, 1997

[30]  Foreign Application Priority Data

Oct. 18, 1996 [HR] Croatia ................................ P970478A

[51] Int. Cl.⁶ .................................................. A61B 17/56
[52] U.S. Cl. ............................................ 606/99; 606/104
[58] Field of Search .............................. 606/99, 100, 104, 606/86; 81/450, 64, 177.8, 177.75; 433/25, 141, 229

[56]  References Cited

U.S. PATENT DOCUMENTS

| | | | |
|---|---|---|---|
| 5,236,289 | 8/1993 | Salyer | 81/177.75 |
| 5,329,834 | 7/1994 | Wong | 81/177.8 |
| 5,391,170 | 2/1995 | McGuire et al. | 606/86 |
| 5,458,603 | 10/1995 | Futch, Sr. | 606/104 |
| 5,464,407 | 11/1995 | McGuire | 606/86 |
| 5,797,918 | 8/1998 | McGuire et al. | 606/104 |

*Primary Examiner*—Guy V. Tucker

[57]  ABSTRACT

The instant invention teaches a surgical implant wrench that includes: a handle; a head for mechanically engaging the handle at an angle relative thereto, that further includes: finger grip indents disposed thereon; and, a first mechanical assembly for rotatably engaging the crown of a surgical implant that is to be surgically implanted into the boney tissue of a patient. The wrench further includes: a second mechanical assembly for selectively varying the angle; a third mechanical assembly for selectively fixing the angle; and, a fourth mechanical assembly including finger grips for mechanically transmitting rotational mechanical force relative to the axis of the handle, from the handle to the first mechanical assembly.

6 Claims, 2 Drawing Sheets

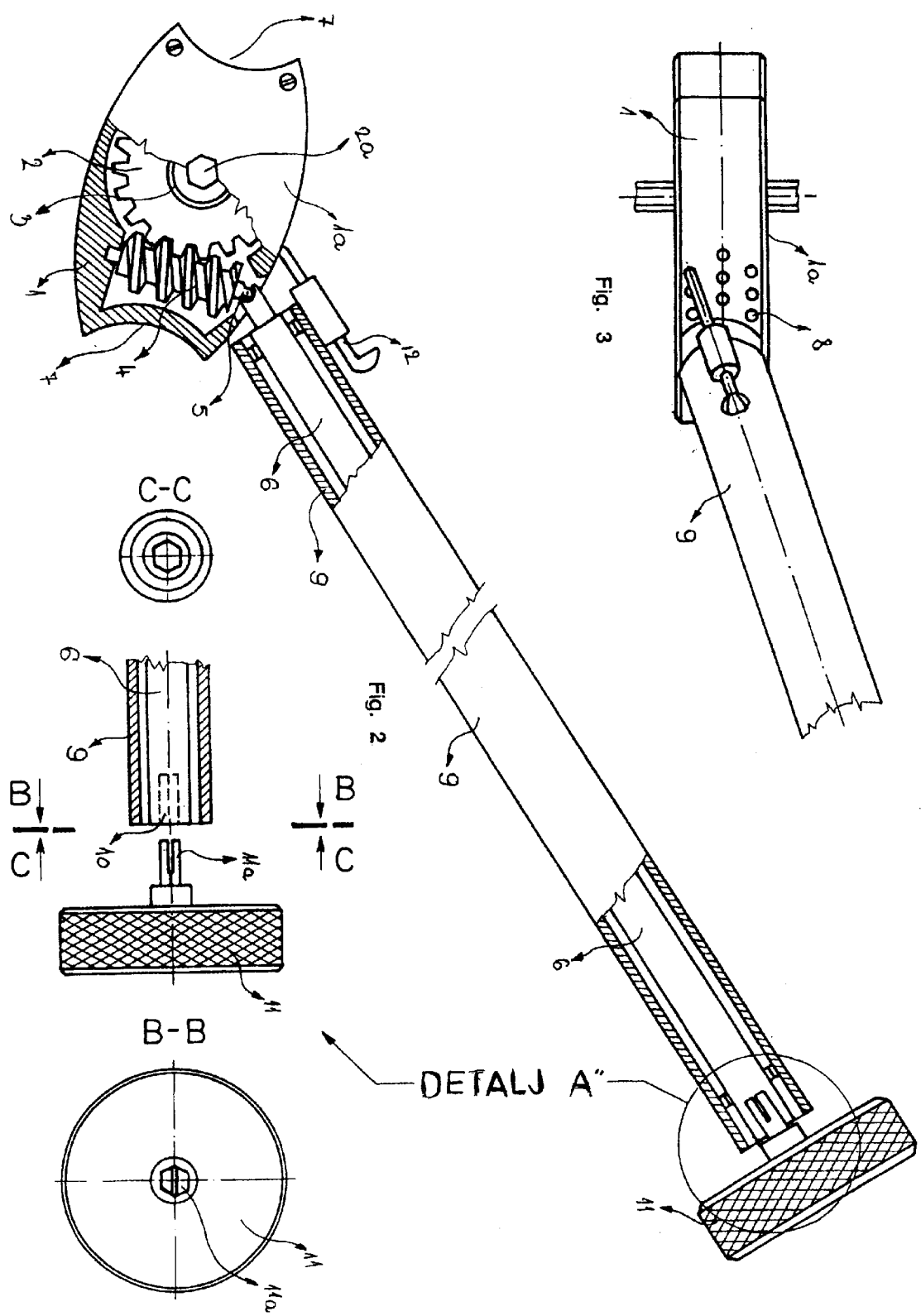

SURGICAL ANGLED SCREWDRIVER

BACKGROUND OF THE INVENTION

The instant invention broadly relates to the field of surgical instruments. More specifically, the invention relates to the field of hand held surgical instruments used for installing surgical implants. Still more specifically, the invention relates to a hand held wrench for installing surgical dental or orthopedic implants such as bolts or screws, into the boney tissues of a patient.

Surgical torque screwdriver devices are well known in the prior art. For instance, U.S. Pat. No. 4,852,386 to Grabovac, et al, teaches a hand-held torque tester for a hand-held torque-limiting tool that includes an elongated horizontal plate with a central longitudinal axis; top and bottom surfaces; front and rear ends and opposite sides; an elongated horizontal longitudinally-extending deflection beam with front and rear ends in spaced relationship above the top surface and parallel with the longitudinal axis of the plate; a vertical mounting pin depending from the front end of the beam and into the plate for free relative rotation therein and against vertical and horizontal displacement relative thereto; a driver part fixed to and projecting rearwardly from the rear end of the beam and having a central vertical drive opening to receive and establish rotary driving engagement with a part of a tool to be tested; a reaction assembly carried by the plate and defining laterally-spaced oppositely-disposed reaction surfaces at opposite sides of the beam adjacent to the rear end thereof; an elongate horizontal pointer with front and rear ends normally in spaced parallel relationship with the beam and having its rear end fixed to the driver and a front end portion projecting forwardly and toward the top surface of the plate forward of the beam; and, a force-indicating scale on and extending laterally of the plate below the front end of the pointer.

U.S. Pat. No. 5,226,906 to Crombie, et al, teaches an apparatus for installing a first part on a second part utilizing a threaded fastener passing through the first part and engaging the second part. The apparatus includes: a body; a drive assembly for applying torque to the threaded fastener. The drive assembly is rotatably mounted in the body and includes a socket assembly for receiving the threaded fastener; and an assembly for holding the first part adjacent to the body with the threaded fastener passing through the first part and received in the socket assembly. The holding assembly is configured and dimensioned to position the first part sufficiently close to the socket assembly so as to retain the threaded fastener therein. The drive assembly is rotatable with respect to the holding assembly. The first part may be installed on the second part without the necessity of a person touching or separately holding the first part after it is held by the holding assembly.

U.S. Pat. No. 5,352,231 to Brumfield, et al, teaches a nut starting tool assembly for driving a nut onto a threaded end of a bone bolt when the bolt is secured in animal bone. The tool assembly includes a shaft having a first end configured for fitting reception on a tool receiving end of a bone bolt, and an opposite second end configured for rotating the shaft. The shaft further incudes a storage assembly at an intermediate portion thereof for reception and temporary storage thereon of a nut to be installed on the threaded end of the bone bolt. The assembly further includes a sleeve coaxially disposed on the shaft and a first end configured for fitting reception on the nut when temporarily stored on the intermediate portion of the shaft; and an opposite second end configured to be manipulated independent of the shaft to move the nut off the storage assembly and drive the nut onto the threaded end of the bone bolt when the nut is received within the first end.

U.S. Pat. No. 5,368,480 to Balfour, et al, teaches a dental tightening torque limit tool holder that includes a tool fixture, a hub and a plurality of torque limit controls.

Universal wrenches which embody universal joints are well known in the prior art. For instance, U.S. Pat. No. 5,458,028 to Cleveland, teaches A universal joint device for interconnecting the handle portion and socket portion of a socket wrench is disclosed. The universal joint device is constructed with grooves for receiving the upper and lower ends of a coil spring which maintains the universal joint in alignment during both tension and compression. The universal joint device is also provided with recessed apertures for receiving washers or similar adjustment devices to allow the device to be customized for additional rigidity or flexibility. Previous universal joint devices are described, for example, in the following U.S. Pat. No. 1,102,863 to Bojas; U.S. Pat. No. 1,324,898 to Hopcraft; U.S. Pat. No. 2,327,821 to Rueb; U.S. Pat. No. 2,499,569 to Cooley; U.S. Pat. No. 3,122,901 to Thompson; U.S. Pat. No. 3,522,713 to Hayes; U.S. Pat. No. 4,065,941 to Aoki; U.S. Pat. No. 4,075,913 to Tye; and U.S. Pat. No. 4,721,493 to Lane; U.S. Pat. No. 4,108,027 to Lenker; U.S. Pat. No. 4,296,654 to Mercer.

The above disclosed prior art surgical implant wrenches: require complicated torque measurement assemblies that add to their cost of production; and/or, can be effectively operated only by a plurality of operators, thus requiring additional man power; and/or, require rotation of a handle about an implant to tighten it, thereby precluding their use in various confined environments.

Thus, despite the foregoing contributions of the prior art, it would nonetheless be desirable to provide the surgical practitioner with an improved surgical implant wrench, wherein the angle between the head and handle of the wrench can be selectively varied and thereafter selectively fixed so as to enable reduced costs of production, operation by single operators, and application to substantially any surgical environment regardless of available operating space requirements.

SUMMARY OF THE INVENTION

The instant invention in large part solves the problems of the prior and fulfills a long felt need by providing novel surgical implant wrench.

The instant invention provides a novel surgical implant wrench having a novel handle and a novel head.

In order that the detailed description that follows may be better understood; and in order for the present contribution to the art may be better appreciated, here are the more important features of the invention as broadly outlined. There are additional features of the invention that will be described hereinafter and which form the subject matter of the appended claims. Those of ordinary skill in the art will appreciate that the conception upon which this disclosure is based may readily be utilized as a basis for the designing of other structures, methods and systems for carrying out the several purposes of the instant invention. It is important, therefore, that the claims be regarded as including such equivalent constructions insofar as they do not depart from the spirit and scope of the instant invention.

Further, the purpose of the instant abstract is to enable the U.S. Patent and Trademark office and the public generally, especially scientists, engineers and practitioners in the art who are not not familiar with patent or legal terms or phraseology, to determine quickly from a cursory inspection of it, the technical disclosure of the patent application. The abstract is neither intended to define the invention of the instant patent application, which is measured by the claims, nor is it intended in any manner to be limiting as to the scope of the instant invention.

In light of the foregoing, it is therefore an object of the instant invention to provide a new and improved surgical implant wrench which has all of the advantages of the prior art and none of its disadvantages.

It is another object of the instant invention to provide a new and improved surgical implant wrench that is more easily and efficiently manufactured and marketed than those of the prior art.

It is another object of the instant invention to provide a new and improved surgical implant wrench which is of a durable and reliable construction.

It is another object of the instant invention to provide a new and improved surgical implant wrench that can be manufactured at a comparably lower cost with regard to both labor and materials, and which accordingly can be sold at a comparably lower cost, thus promoting commerce.

It is a further object of the instant invention to provide a new and improved surgical implant wrench that provides at least some of the advantages of the prior art schemes, while simultaneously eliminating at least some of the disadvantages of them.

It is a further object of the instant invention to provide a new and improved surgical implant wrench that enables its use by a single operator.

It is an object of the instant invention to provide a surgical implant wrench that enables effective finger sensing of the torque that is applied in tightening a surgical implant.

It is a further object of the instant invention to provide a surgical implant wrench having a handle that requires no rotation about a surgical implant in order to tighten it.

It is a further object of the instant invention to provide a surgical implant wrench that has application to substantially all surgical environments regardless of available operating space requirements.

It is a further object of the instant invention to provide a surgical implant wrench that can be effectively operated to tighten a surgical implant by the hand sensed torque applied by a single operator.

Other objects, features, and advantages of the instant invention, in its details of construction and arrangement of parts, will be seen from the above, from the following description of the preferred embodiment when considered in light of the drawings and the appended claims.

BRIEF DESCRIPTION OF THE DRAWINGS

FIG. 2 shows a partial cutaway plan view of the instant surgical implant wrench, further showing sections "B—B" and "C—C."

FIG. 3 shows a fragmentary side view of the instant surgical implant wrench.

DETAILED DESCRIPTION OF THE INVENTION

Surgical Implants

Figure 1:
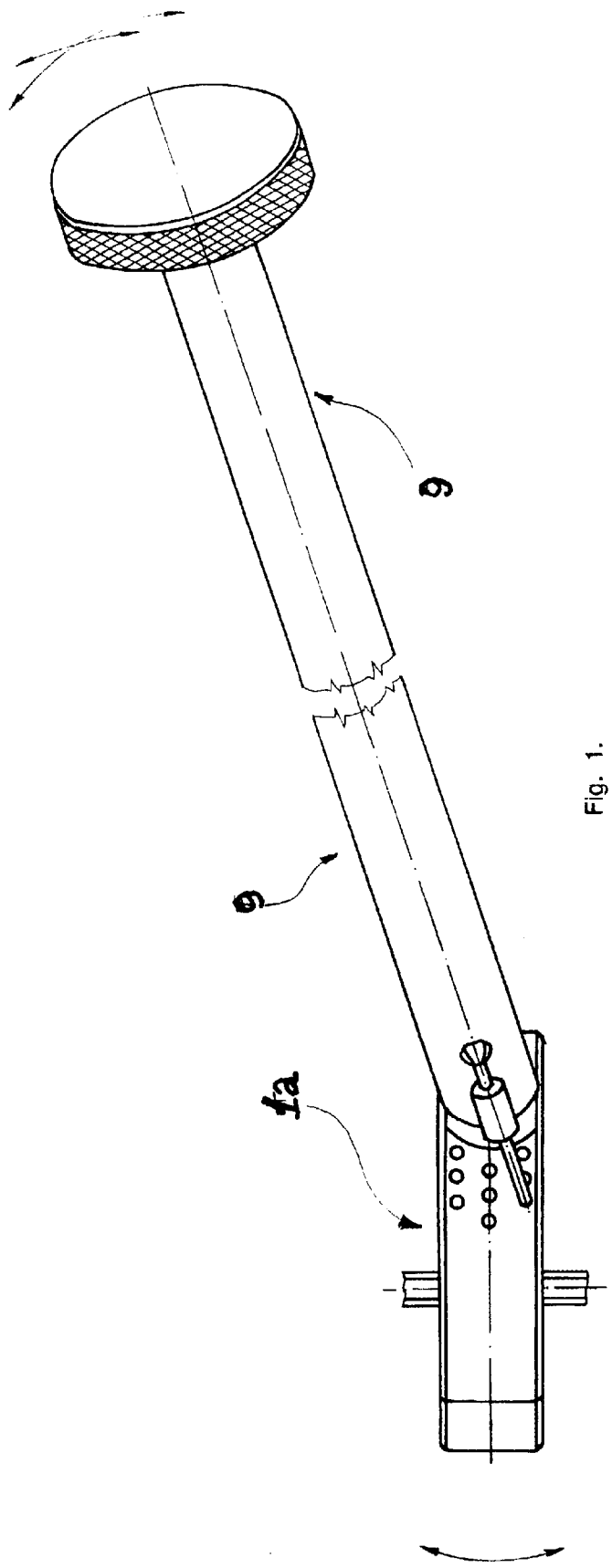
FIG. 1 shows an isometric side view of the surgical implant wrench of the present invention.

Because of their superior compatibility with bone tissue and their tendency to form a firm attachment directly with bone tissue, titanium and titanium alloys are typically used as the preferred material of construction for implants used in the practice of dental and orthopedic surgery. The precise mechanism which accounts for this superiority are not at present fully understood.

The standard surgical technique for fixing a surgical dental or orthopedic implant involves a two-stage process. In the first stage the soft tissue covering the bone tissue is opened and a base pan of the implant is placed in the bone tissue. The soft tissue is closed and the implant is left to osseointegrate for a comparatively long period of time. In the second stage the soft tissue is re-opened and the load-bearing parts of the implant are attached to the base part. This technique is not without its disadvantages. First of all, the substantial period of time required for osseointegration can result in substantial discomfort to the patient. Secondly, as a general rule of orthopaedics, plural operations on the same bone site is not advisable. Thus, it would be preferable to conduct the foregoing operation in one stage. A vital consideration in reducing the operation to a single stage is the time period required for the osseointegration process to generate a sufficiently strong bone tissue-implant interface. Complications frequently develop in those cases where the quality of the bone is poor or the available space is limited. Typically such problem sites are: the upper jaw or in the posterior parts of the lower jaw above the nerve. It is desirable at these sites, to stimulate the regeneration of the bone tissue around the implant.

Several methods have been proposed by the prior art for treating implants made of titanium so as to promote more complete attachment of the implant to the bone structure. Several of these methods involve altering the topography of the implant. One of these methods proposes the creation of large irregularities on the implant surface in order to obtain a better mechanical retention and to increase the area of attachment by various means such as plasma spraying, blasting or etching. Although retention may be improved, the time necessary for the osseointegration process is increased since the bone tissue must grow into the irregularities in the surface.

Other methods contemplate the alteration of the chemical properties of the implant surface so as to promote the formation of the bone-implant interface. One such method involves the application of a layer of ceramic material such as hydroxyapatite to the implant surface, inter alia in order to stimulate the regeneration of the bone tissue. Ceramic coatings however may be brittle and may flake or break off from the implant surface, which may in turn lead to the ultimate failure of the implant.

Dental Implants

Although the instant invention also contemplates orthopedic bone implants, it is more preferably directed to dental bone implants.

There are basically two types of dental implants. Those that sit on top of the jaw bone, but under the gums, and those that fit into the jawbone similar to the root of a natural tooth. Each type offers solid, non-mobile support for replacement teeth which act and feel like natural teeth. Since both types are attached to the patient's jawbone they can provide distinct advantages over traditional methods of replacing missing teeth.

There are generally four types of dental bone grafts used: autografts are those where the bone to be grafted to the jaw is taken, or harvested, from the patient's own body. The area where the bone is harvested from, known as the donor site, is usually the mouth or the hip. This is the patient's own bone and is very compatible with the patient's body. Autografts are generally the best graft technique and usually result in the greatest regeneration of missing jawbone. Allografts are taken from human donors. Many countries have donor programs where you can specify that in the event of the patient's death, parts may be harvested from the patient's body to save or improve the life of others. Heart transplants are one type of allograft. This can represent one of the greatest "gifts" you can ever give. Bone obtained in this manor undergoes rigorous tests and sterilization. The patient's body "converts" the donor bone into the patient's natural bone, thereby rebuilding the patient's resorbed jawbone.

Xenografts are harvested from animals. The animal bone, most commonly bovine (cow), is specially processed to make it biocompatible and sterile. It acts like a "filler" which in time the patient's body will replace with natural bone. After this replacement process is complete dental implants may be placed to support teeth.

Alloplastic grafts are inert, man made synthetic materials. The modern artificial joint replacement procedure uses metal alloplastic grafts. For bone replacement a man made material that mimics natural bone is used. Most often this a form of calcium phosphate. Depending on how it is made, it may be "resorbable" or "non-resorbable". That is, the patient's body may or may not replace the alloplastic graft with the patient's natural bone. In those cases where it is not replaced it acts as a lattice or scaffold upon which natural bone is built. In either case, the end result is to create enough bone for the placement of dental implants.

There are many implants available, each designed for a specific function. Most are made of titanium, an inert metal which has been proven to be effective at fusing with living bone, a process known as "osseointegration". The cylindrical or screw type implant, called "root form", is similar in shape to the root of a tooth with a surface area designed to promote good attachment to the bone. It is the most widely used design and generally placed where there is plentiful width and depth of jawbone. Where the jawbone is too narrow or short for immediate placement of root form implants the area may be enhanced with bone grafting to allow for their placement.

When the jawbone is too narrow and not a good candidate for bone grafting, a special narrow implant, called "plate form", can be placed into the bone. In cases of advanced bone loss, the "subperiosteal" implant, may be prescribed. It rests on top of the bone but under the gums.

The actual implant procedure involves the surgical placement of the implant or implants, a healing period (osseointegration) and implant restoration to replace the missing tooth or teeth. The treatment may be a cooperative effort between a surgical dentist who actually places the implant and a restorative dentist who designs, prescribes and inserts the final replacement teeth. Some dentists have advanced training and provide both of these services.

Root form implants are the closest in shape and size to the natural tooth root. They are commonly used in wide, deep bone to provide a base for replacement of one, several or a complete arch of teeth. After application of anesthetic, the patient's dentist will expose the area of the jawbone to be implanted and prepare the bone to accept the implant. The number of incisions and bone preparations depends upon the number of implants (and teeth) being placed. The implant is carefully set into place and the gums are closed with several stitches. The healing period usually varies from as few as three months to six or more. During this time osseointegration occurs. The bone grows in and around the implant creating a strong structural support. In fact, this bond can be even stronger than the original tooth's. When healing is complete, the patient's implant is uncovered and an extension or abutment is attached to it. Now the implant and abutment act as a solid unit ready to support the patient's new tooth or teeth.

Plate form implants are usually used when the bone is so narrow it may not be suitable for the root form implant and the area is not suitable for bone grafting. The plate form implant is flat and long so it can fit into the narrow jawbone. After application of anesthetic, the patient's dentist will expose the area of the jawbone to be implanted and prepare the bone to accept the shape of the implant. The number of incisions depends upon the number of implants being placed. The implant is carefully set into place and the gums are closed with several stitches. Like root form implants, there is usually a healing period for osseointegration, although some plate form implants are designed for immediate restoration.

With very advanced jawbone resorption there may not be enough bone width or height for the root form or plate form implant. In these cases the subperiosteal implant may be prescribed. The subperiosteal implant is custom made and designed to sit on top of the bone, but under the gums. There are two methods for its placement. After application of anesthetic, the patient's dentist will expose the jawbone and take an impression or model of the bone using special materials. This model is used by a dental laboratory to carefully create the custom implant to fit the patient's jaw. A second procedure is then carried out where the jawbone is exposed and the implant placed. The gums are closed with several stitches and replacement teeth are put into place.

For the "single surgery" method, the patient's dentist will order a special CAT scan of the patient's jawbone. Using the CAT scan data and advanced computer modeling techniques, a model of the patient's jawbone is constructed. This model is used by a dental laboratory to fabricate the custom subperiosteal implant to fit the patient's jaw. A surgical procedure is then carried out where the jawbone is exposed and the implant placed. The gums are closed with several stitches and the replacement teeth are put into place.

Bone Implants

In orthopedic and traumatologic surgery, particularly those in the case of fractures, bone fragments to be joined are often fixed together by means of bone screws or bone implants in conjunction with such screws. A bone screw should be tightened to such an extend that on the one hand, the bone fragments are pressed together as tightly as possible and on the other hand the bone fragments, the screw and the respective threads in the bone and on the screw are not damaged. A screw should therefore be tightened until the tightening torque has reached an optimum value slightly below that at which the threads are stripped.

The current practice is for surgeons to tighten the screws by feel. There have been tests carried out to determine the resultant torque values wherein surgeons have used a screwdriver with a torque measuring transducer. The results of these tests have been published in the paper "Dosierung des Drehmoments beim Einsetzen von Knochenschrauben" ("Dosage of Torque for the Insertion of Bone Screws") by J. Cordey, W. Widmer, A. Rohner and S. M. Perren in 115 Zeitschrift fur Orthopadie und ihre Grenzgebiete ("Journal of Orthopaedics and Allied Fields"), pp. 601&602 (1977.)

For surgeons who do not yet have much experience it is difficult to tighten the screws by feel just enough for the torque obtained at the end of tightening to be approximately equal to the optimum value. The surgeons could naturally use a screwdriver which limits the tightening torque for the screws to a pre-set definite maximum value. This would not be practical, however, since the various torque values at which the threads are stripped depend on the individual features of the bone and vary considerably from case to case, from bone to bone in the same individual and from location to location in the same bone. Tests in which screws with a diameter of 4.5 mm were screwed into the tibiae of fifteen different human cadavers have shown that the torque value at which the threads are stripped vary between about 1 and 7 Newton meters. If the torque were limited to a fixed value, this value would therefore have to be such that the threads would not be stripped even in the case of the bones with the lowest strength. This would then mean that when screws are inserted into bones of greater strength the torque would be far below the optimum for that bone.

Presently known and most widely utilized implants consist of any component of metal which is to be inserted in the bone and are shaped in a form of a plate, needle, screw or the like, and are predicated on a purely mechanical intermeshing with the bone in order to attain an anchoring of the prosthesis on the bone. In the interim it has been recognized that numerous technical requirements must be concurrently fulfilled with respect to the material in order to achieve a durable stable implantation. The employed materials must be biocompatible with the bone and the shaping of the implants and the mechanical properties of the material must afford a biologically correct loading and introduction of forces since, otherwise, the bone will react through degeneration and, finally, through loosening of the implant. It has further been recognized that the implant must in all regions evidence a direct, durable, osseous-like connection with the bone and cannot be encapsulated relative to the bone through a connective tissue membrane.

For this purpose, bioactive materials have become known in more recent times which effect a connective tissueless growing together of the bone with the surface of the material of the component. With such materials this relates, for example, to calcium phosphates of predetermined composition wherein there takes place a direct connective tissueless growing together of the bone with the material (Koster, "Experimenteller Knochenersatz durch resorbierbare Calciumphosphatkeramik", Langenbecks Archiv fur Chirurgie 341, 77–86 (1976). These calcium phosphates are decomposable in the biological environment, in essence, they are absorbed by the cells which are active in the bone transformation, and thereby fulfill the predetermined basic biochemical condition, however, they do not come into consideration as a single material in a prosthesis which is permanently implanted due to a lack of an adequate inherent strength and due to a lack of a durable anchoring between the material of the anchoring component and the bone, because of the given reabsorbability.

In order to create a permanent anchoring for extensively loaded implants which will lead to a really permanent interconnection between the prosthesis and the tissue, it has become known from German-Laid Open Patent Application No. 26 20 907 that the anchoring of the prosthesis can be constructed as a prosthesis shaft coating from a plastic material which is mechanically and chemically stable in the environment of the body, and to so deposit therein ceramic calcium phosphate in a particulate form of predetermined particle size diameter so that there is produced a generally porous matrix of plastic material during the reabsorption of the ceramic components on whose inner pore surfaces there remain bioactivated residues of the ceramic.

In accordance with another proposal for an implantable tooth root as disclosed in German-Laid Open Patent Application No. 27 33 394, this essentially consists of a biostable polymer matrix which is compatible with human cell tissue, in which there are deposited the reabsorbable bioreactive calcium phosphate in a finely-dispersed form, which are encompassed by a thin, porous layer of nonreabsorbable calcium phosphate, and in which there is inserted a core as a connecting element for the mounting of a dental superstructure.

However, some hesitations exist in connection with the utilization of plastic materials in the form of a polymer matrix as a carrier member for the ceramic calcium phosphate although, at this time, they are still well employed in practice. Polymer plastics frequently also include monomers in other deleterious materials which in implants, after respective aging, can lead to exchange reactions with the tissue. Moreover, a plastic material carrier member does not allow for a sufficiently precise shaping and mechanical working in order to enable the construction of an implant equipped with a plastic material support member for the most different purposes, such as bone and joint protheses, or also for bone connecting elements, such as screws, splints and the like.

Implants are known to be used in orthopedics and dentistry in various sizes and shapes. Among the larger ones are the prostheses used to replace the spherical element in the upper joint of the hip bone or femur, among the smaller ones are pins screwed into jaw bones for building artificial teeth. An implant of this kind is frequently made of one of the metals or elements titanium, zirconium, niobium or tantalum, or of a tissue-compatible alloy having one of the aforementioned elements as its main component. A common problem with such implants consists in the necessity of implementing the measures required for the bone substance to establish a speedy and lasting bond or connection with the contact surface of the implant. Other terms used in the art for this process include "implant anchoring" and "osseointegration".

With reference to bone implants, the following statements were made in the Abstract of a Study by the Work Committee for Implants of the German Society for Materials Testing, made public in Berlin on Nov. 17, 1987:

"Combined tension and histomorphometric tests have shown that smooth contact surfaces of titanium implants do not provide adequate interfaces that would resist tension forces. Contact surface roughnesses of more than 20 mum are required if a tension-resistant bone implant bond or connection is to be built. Uniform geometrical surface patterns as well as non-uniform porous designs are capable of improving the tension strength of the bone-titanium interface or bond, especially if additional sandblasting is applied."

It is customary nowadays to coat the contact surface of an implant with a titanium plasma coat, or to produce a surface roughness thereon by sandblasting or by threading said contact surface. Of common knowledge are both the drawbacks of the surfaces so treated and the fact that contact surface roughness of this kind is required for achieving adequate adhesion between bone and implant. Such drawbacks essentially consist in the fact, that the mechanically brittle plasma layer has a tendency to break or peel off, and in that the surfaces roughened by sandblasting become contaminated by the blasted grains, most often corundum. Attempts made to subsequently to clean the contact surface by means of a pickling or corrosive solution such as hydrofluoric acid plus nitric acid (HF+HNO$_3$) resulted in a substantially less perfect intergrowth of bone substance and implant, and weaker anchoring of the implant in the bone through its contact surface.

Terms used in this specification are generally based on definitions in METALS HANDBOOK, desk edition, by Boyer and Gall, American Society for Metals, Metals Park, Ohio, 1985. According to this text (pages 27.20–27.25), roughness, one of the four elements of surface texture, is the most commonly used surface parameter. Further, surface measuring devices generally indicate the roughness, but do not indicate the physical character of the surface and in effect, several surfaces can be quite different in appearance and still yield similar roughness values. Among roughness parameters are the maximum peak-to-valley height ($R_t$), which can be determined by a surface measuring device, and peak count ($P_c$), which is the number of peak/valley pairs per linear unit of surface and the reciprocal of which is roughness spacing (RS). Thus, $R_t$ concerns perpendicular distances, while RS concerns horizontal distances and together these parameters provide a more accurate picture of the surface texture than either parameter alone.

The Drawings

Reference is now made to the instant drawings to more specifically describe the present invention. FIG. 1 shows a side view of the surgical implant wrench of the invention, specifically depicting handle 9 and head 1.

FIG. 2 shows a partial cutaway plan view of the instant surgical implant wrench, further showing sections "B—B" and "C—C." Depicted in FIG. 2, is a surgical implant wrench that includes a handle 9, a head 1a for mechanically engaging the handle 9 at a preselected angle relative thereto. The head 1a further includes finger grip indents 7 disposed thereon; and, a first mechanical assembly, that includes a worm gear 4 that drives a flat gear 2, fixedly attached to an implant engagement element 2a, for rotatably engaging the crown of a surgical implant. The implant can be either a dental implant or a orthopedic implant, that is to be surgically implanted into the boney tissue of a patient. Also shown is a second mechanical assembly for selectively varying the angle of the handle 9 relative to the head 1a. This second mechanical assembly also includes a universal joint 5 disposed between the handle 9 and the head 1a; for the angular transmission of work to worm gear 4, flat gear 2 and implant engagement element 2a. The work required to tighten or untighten an implanted is inputted by the fingers of the operator through the axial rotation of a knurled knob 3 to the axial rotatable inner shaft 6. The universal joint 5 is preferably the ball and socket type. However, other types, such as that similar to that type included in the drive shaft of an automobile, is suitable. The instant surgical implant wrench also includes a third mechanical assembly for selectively fixing the angle of the handle 9 relative to the head 1a.

FIG. 2 shows in clearer detail the third mechanical assembly of the instant surgical implant wrench. This assembly includes an array of bored holes 8 (as shown in FIG. 3) disposed on the periphery of the head at about where the handle engages the head; and, a slidable pin 12 mounted on the handle 9 for selectively inserting into one of the bored holes 8 sufficient to selectively fix the angle. Preferably, pin 12 is spring biased within the tubular member that otherwise fixes it to handle 9. Sections "B—B" and "C—C" show respectively, a cross sections of the knurled knob 11; and, the handle 9 and rotatable inner shaft 6; as well as the details wherein the knurled knob 11 is fixedly attached to rotatable inner shaft 6.

Operation of the Surgical Implant Wrench

In order to use the instant surgical implant wrench, the practitioner first adjusts the angle of the handle 9 relative to the head 1a by manipulating pin 12 into the appropriate bored hole 8. The practitioner then grasps the head of the wrench by finger grip indents 7 and engages a positioned implant with the implant engagement element 2a. The free hand of the practitioner is thereafter employed to apply work to rotate the knurled knob 11 in the appropriate angular direction to either tighten or loosen the positioned implant.

Definitions

The term "crown" as used herein refers to any portion of a surgical implant that is designed to be engaged by a tightening device, to be screwed, bolted or otherwise fixed into the boney tissues of a patient.

The term "anchor" and its variants, as used herein, refer to that part of any implant prosthesis that is fixed into the bone tissue of a living patient.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. A surgical implant wrench comprising:
   a handle;
   a head for mechanically engaging said handle at an angle relative thereto, including,
      finger grip indents disposed thereon; and,
      a first mechanical assembly for rotatably engaging the crown of a surgical implant that is to be surgically implanted into the boney tissue of a patient;
   a second mechanical assembly for selectively varying said angle;
   a third mechanical assembly for selectively fixing said angle; and,
   a fourth mechanical assembly including finger grips for mechanically transmitting rotational mechanical force relative to the axis of said handle, from said handle to said first mechanical assembly.

2. The surgical wrench of claim 1, wherein said surgical implant is selected from the group consisting of: a dental implant and a orthopedic implant.

3. The surgical wrench of claim 1, wherein said second mechanical assembly further comprises a universal joint disposed between said handle and said head, further functioning for enabling said transmitting.

4. The surgical wrench of claim 1, wherein said third mechanical assembly further comprises:
   and array of bored holes disposed on the periphery of said head where said handle engages said head; and,
   a slidable pin mounted on said handle for selectively inserting into one of said bored holes sufficient to selectively fix said angle.

5. A surgical implant wrench comprising:
   a handle;

a head for mechanically engaging said handle at an angle relative thereto, including,
  finger grip indents disposed thereon; and,
  a first mechanical assembly for rotatably engaging the crown of a surgical implant, selected from the group consisting of: a dental implant and a orthopedic implant; that is to be surgically implanted into the boney tissue of a patient;
a second mechanical assembly for selectively varying said angle, including:
  a universal joint disposed between said handle and said head, further functioning for enabling said transmitting;
a third mechanical assembly for selectively fixing said angle including:
  an array of bored holes disposed on the periphery of said head where said handle engages said head; and,
  a slidable pin mounted on said handle for selectively inserting into one of said bored holes sufficient to selectively fix said angle; and,
a fourth mechanical assembly including finger grips for mechanically transmitting rotational mechanical force relative to the axis of said handle, from said handle to said first mechanical assembly.

6. A method for installing a surgical implant in the boney tissue of a patient, comprising:

providing a surgical implant wrench that includes: a handle; a head for mechanically engaging said handle at an angle relative thereto, including, finger grip indents disposed thereon; and, a first mechanical assembly for rotatably engaging the crown of a surgical implant that is to be surgically implanted into the boney tissue of a patient; a second mechanical assembly for selectively varying said angle; a third mechanical assembly for selectively fixing said angle; and, a fourth mechanical assembly including finger grips for mechanically transmitting rotational mechanical force relative to the axis of said handle, from said handle to said first mechanical assembly;

positioning said implant at a desired point on said boney tissue;

engaging said crown with said first mechanical assembly;

varying said angle to a desired inclination;

fixing said angle;

causing the operator of said wrench to grasp said head at said finger grip indents with one hand;

causing said operator to grasp said finger grips of said fourth mechanical assembly with the other hand of said operator; and, causing said operator to rotate said fourth mechanical assembly sufficient to enable installation of said implant.

* * * * *